(12) United States Patent  
McAlister

(10) Patent No.: US 8,624,072 B2  
(45) Date of Patent: Jan. 7, 2014

(54) CHEMICAL REACTORS WITH ANNULARLY POSITIONED DELIVERY AND REMOVAL DEVICES, AND ASSOCIATED SYSTEMS AND METHODS

(75) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/481,682

(22) Filed: May 25, 2012

(65) Prior Publication Data

US 2013/0149208 A1    Jun. 13, 2013

Related U.S. Application Data

(63) Continuation of application No. 13/026,990, filed on Feb. 14, 2011, now Pat. No. 8,187,549.

(60) Provisional application No. 61/304,403, filed on Feb. 13, 2010.

(51) Int. Cl.  
*C07C 1/00* (2006.01)

(52) U.S. Cl.  
USPC .................. 585/240; 422/186.3; 588/400

(58) Field of Classification Search  
USPC ............ 422/186, 186.3; 126/569, 572, 600; 585/240; 588/400; 204/157.15; 201/21  
See application file for complete search history.

(56) References Cited

U.S. PATENT DOCUMENTS

| | | | |
|---|---|---|---|
| 3,613,792 A | 10/1971 | Hyde et al. | |
| 3,633,372 A | 1/1972 | Kimmel et al. | |
| 3,662,832 A | 5/1972 | Keeler et al. | |
| 3,788,389 A | 1/1974 | Waters | |
| 3,807,491 A | 4/1974 | Van Hulsen | |
| 3,840,068 A | 10/1974 | Waters | |
| 3,882,937 A | 5/1975 | Robinson | |
| 3,936,652 A | 2/1976 | Levine | |
| 3,986,362 A | 10/1976 | Baciu | |
| 4,019,868 A | 4/1977 | Sebacher et al. | |

(Continued)

FOREIGN PATENT DOCUMENTS

| CN | 101042261 A | 9/2007 |
|---|---|---|
| CN | 101091900 A | 12/2007 |

(Continued)

OTHER PUBLICATIONS

U.S. Appl. No. 13/027,208, filed Feb. 14, 2011, now U.S. Patent No. 8,318,131, issued Nov. 27, 2012 and titled Chemical Processes and Reactors for Efficiently Producing Hydrogen Fuels and Structural Materials, and Associated Systems and Methods.

(Continued)

*Primary Examiner* — Nina Bhat  
(74) *Attorney, Agent, or Firm* — Perkins Coie LLP

(57) ABSTRACT

Chemical reactors with annularly positioned delivery and removal devices, and associated systems and methods. A reactor in accordance with a particular embodiment includes a reactor vessel having a light-transmissible surface proximate to a reaction zone, and a movable reactant delivery system positioned within the reactor vessel. The reactor can further include a product removal system positioned within the reactor vessel and positioned annularly inwardly or outwardly from the delivery system. A solar concentrator is positioned to direct solar radiation through the light-transmissible surface to the reaction zone.

20 Claims, 6 Drawing Sheets

(56) References Cited

U.S. PATENT DOCUMENTS

| | | | |
|---|---|---|---|
| 4,053,576 A | 10/1977 | Fletcher | |
| 4,070,861 A | 1/1978 | Scragg et al. | |
| 4,099,489 A | 7/1978 | Bradley | |
| 4,138,993 A | 2/1979 | Conley | |
| 4,172,506 A | 10/1979 | Terry | |
| 4,229,184 A | 10/1980 | Gregg | |
| 4,257,239 A | 3/1981 | Partin | |
| 4,343,338 A | 8/1982 | Hart | |
| 4,382,189 A | 5/1983 | Wilson | |
| 4,386,801 A | 6/1983 | Chapman et al. | |
| 4,455,045 A | 6/1984 | Wheeler | |
| 4,549,528 A * | 10/1985 | Gibson | 588/306 |
| 4,601,508 A | 7/1986 | Kerian | |
| 4,611,847 A | 9/1986 | Sullivan | |
| 4,620,580 A | 11/1986 | Groezinger et al. | |
| 4,706,651 A | 11/1987 | Yudow | |
| 4,746,160 A | 5/1988 | Wiesemeyer | |
| 4,921,580 A | 5/1990 | Martes et al. | |
| 4,978,162 A | 12/1990 | Labbe | |
| 5,058,945 A | 10/1991 | Elliott, Sr. et al. | |
| 5,119,897 A | 6/1992 | Moriwake | |
| 5,132,090 A | 7/1992 | Volland | |
| 5,222,698 A | 6/1993 | Nelson et al. | |
| 5,280,990 A | 1/1994 | Rinard | |
| 5,315,868 A | 5/1994 | Jacobi et al. | |
| 5,348,774 A | 9/1994 | Golecki et al. | |
| 5,407,245 A | 4/1995 | Geropp | |
| 5,498,059 A | 3/1996 | Switlik | |
| 5,560,443 A | 10/1996 | DuBose | |
| 5,618,134 A | 4/1997 | Balch | |
| 5,647,877 A | 7/1997 | Epstein | |
| 5,882,382 A | 3/1999 | Hachisuka et al. | |
| 5,986,429 A | 11/1999 | Mula, Jr. | |
| 6,012,065 A | 1/2000 | Boucher et al. | |
| 6,068,328 A | 5/2000 | Gazdzinski | |
| 6,081,183 A | 6/2000 | Mading et al. | |
| 6,089,224 A | 7/2000 | Poulek | |
| 6,092,861 A | 7/2000 | Whelan | |
| 6,155,212 A | 12/2000 | McAlister | |
| 6,200,069 B1 | 3/2001 | Miller | |
| 6,216,599 B1 | 4/2001 | Cavanagh | |
| 6,220,193 B1 | 4/2001 | Dilks | |
| 6,242,752 B1 | 6/2001 | Soma et al. | |
| 6,309,010 B1 | 10/2001 | Whitten | |
| 6,378,932 B1 | 4/2002 | Fasel et al. | |
| 6,409,252 B1 | 6/2002 | Andrus | |
| 6,464,755 B2 | 10/2002 | Nakanishi et al. | |
| 6,502,533 B1 | 1/2003 | Meacham | |
| 6,508,209 B1 | 1/2003 | Collier, Jr. | |
| 6,531,704 B2 | 3/2003 | Yadav et al. | |
| 6,534,210 B2 | 3/2003 | Luken et al. | |
| 6,571,747 B1 | 6/2003 | Gerstweiler | |
| 6,585,785 B1 | 7/2003 | Warren et al. | |
| 6,630,267 B2 | 10/2003 | Badding et al. | |
| 6,749,043 B2 | 6/2004 | Brown et al. | |
| 6,756,140 B1 | 6/2004 | McAlister | |
| 6,838,782 B2 | 1/2005 | Vu | |
| 6,854,788 B1 | 2/2005 | Graham | |
| 6,886,249 B2 | 5/2005 | Smalc | |
| 6,897,575 B1 | 5/2005 | Yu | |
| 6,919,062 B1 | 7/2005 | Vasileiadis et al. | |
| 6,923,004 B2 | 8/2005 | Chandran et al. | |
| 6,926,345 B2 | 8/2005 | Ortega et al. | |
| 6,979,049 B2 | 12/2005 | Ortega et al. | |
| 7,014,737 B2 | 3/2006 | Harutyunyan et al. | |
| 7,033,570 B2 * | 4/2006 | Weimer et al. | 423/650 |
| 7,140,181 B1 | 11/2006 | Jensen et al. | |
| 7,152,908 B2 | 12/2006 | Shahbazi | |
| 7,165,804 B2 | 1/2007 | Shahbazi | |
| 7,179,383 B1 | 2/2007 | Porter et al. | |
| 7,185,944 B2 | 3/2007 | Shahbazi | |
| 7,207,620 B2 | 4/2007 | Cosgrove et al. | |
| 7,210,467 B2 | 5/2007 | Kweon et al. | |
| 7,211,905 B1 | 5/2007 | McDavid, Jr. | |
| 7,237,827 B2 | 7/2007 | Shahbazi | |
| 7,243,980 B2 | 7/2007 | Vala | |
| 7,250,151 B2 | 7/2007 | Tonkovich et al. | |
| 7,285,350 B2 | 10/2007 | Keefer et al. | |
| 7,293,533 B2 | 11/2007 | Hemsath | |
| 7,337,612 B2 | 3/2008 | Skinnes et al. | |
| 7,397,141 B2 | 7/2008 | Gouker | |
| 7,420,004 B2 | 9/2008 | Hardy et al. | |
| 7,449,158 B2 | 11/2008 | Haueter et al. | |
| 7,527,094 B2 | 5/2009 | McKinzie et al. | |
| 7,568,479 B2 | 8/2009 | Rabinowitz | |
| 7,628,137 B1 | 12/2009 | McAlister | |
| 7,692,170 B2 | 4/2010 | Gaus et al. | |
| 7,713,642 B2 | 5/2010 | Warner et al. | |
| 7,714,258 B2 | 5/2010 | Dalton | |
| 7,753,122 B2 | 7/2010 | Curlett | |
| 7,788,924 B2 | 9/2010 | Hines | |
| 7,789,182 B2 | 9/2010 | Bradley et al. | |
| 7,808,121 B1 | 10/2010 | Glynn | |
| 7,884,308 B1 | 2/2011 | Mejia | |
| 7,943,045 B2 | 5/2011 | Rohrich et al. | |
| 7,955,478 B2 | 6/2011 | McClure | |
| 7,971,861 B2 | 7/2011 | Soininen | |
| 8,043,592 B2 | 10/2011 | Krass | |
| 8,053,916 B2 | 11/2011 | Edwards et al. | |
| 8,083,520 B2 | 12/2011 | Mueller et al. | |
| 8,187,549 B2 * | 5/2012 | McAlister | 422/186 |
| 8,187,550 B2 * | 5/2012 | McAlister | 422/186 |
| 8,220,539 B2 | 7/2012 | Vinegar et al. | |
| 8,318,100 B2 * | 11/2012 | McAlister | 422/110 |
| 8,449,634 B2 | 5/2013 | Tamura et al. | |
| 2003/0008183 A1 | 1/2003 | Hsu | |
| 2004/0200618 A1 | 10/2004 | Piekenbrock | |
| 2004/0219737 A1 | 11/2004 | Quon | |
| 2004/0253168 A1 | 12/2004 | Chu | |
| 2004/0265448 A1 | 12/2004 | Shiau et al. | |
| 2004/0266615 A1 | 12/2004 | Watson et al. | |
| 2005/0029120 A1 | 2/2005 | Bar-Gadda | |
| 2005/0272856 A1 | 12/2005 | Cooper et al. | |
| 2006/0005738 A1 | 1/2006 | Kumar | |
| 2006/0005739 A1 | 1/2006 | Kumar | |
| 2006/0048808 A1 | 3/2006 | Ruckman et al. | |
| 2007/0031718 A1 | 2/2007 | Fujimura et al. | |
| 2007/0065686 A1 | 3/2007 | Fan et al. | |
| 2007/0138006 A1 | 6/2007 | Oakes et al. | |
| 2007/0191664 A1 | 8/2007 | Hershkowitz et al. | |
| 2007/0205298 A1 | 9/2007 | Harrison et al. | |
| 2008/0086946 A1 | 4/2008 | Weimer et al. | |
| 2008/0175766 A1 * | 7/2008 | Mankins et al. | 422/186 |
| 2008/0295883 A1 | 12/2008 | Ducellier et al. | |
| 2009/0206666 A1 | 8/2009 | Sella et al. | |
| 2009/0258278 A1 | 10/2009 | Steinberg | |
| 2009/0313886 A1 * | 12/2009 | Hinman et al. | 44/302 |
| 2010/0000874 A1 * | 1/2010 | Hinman et al. | 205/340 |
| 2010/0043404 A1 | 2/2010 | Hebbale et al. | |
| 2010/0107994 A1 | 5/2010 | Moriarty et al. | |
| 2010/0140950 A1 | 6/2010 | Pitre | |
| 2010/0242352 A1 * | 9/2010 | Perkins et al. | 44/639 |
| 2011/0061295 A1 | 3/2011 | McAlister | |
| 2011/0061383 A1 | 3/2011 | McAlister | |
| 2011/0315539 A1 * | 12/2011 | Zadik et al. | 202/99 |
| 2012/0118878 A1 | 5/2012 | Kim et al. | |

FOREIGN PATENT DOCUMENTS

| | | |
|---|---|---|
| CN | 101597025 A | 12/2009 |
| EA | 200702287 A1 | 4/2008 |
| EP | 1658892 A1 | 5/2006 |
| JP | 2001181846 A | 7/2001 |
| JP | 2001262353 A | 9/2001 |
| JP | 03215670 B2 | 10/2001 |
| JP | 2003040601 A | 2/2003 |
| JP | 2003166059 A | 6/2003 |
| JP | 2005511467 A | 6/2003 |
| JP | 2005021876 A | 1/2005 |
| JP | 2005213069 A | 8/2005 |
| JP | 2007254180 A | 10/2007 |
| JP | 2010003568 A | 1/2010 |
| JP | 2010006653 A | 1/2010 |
| RU | 2011864 C1 | 4/1994 |

(56) References Cited

FOREIGN PATENT DOCUMENTS

| | | |
|---|---|---|
| RU | 2120913 C1 | 10/1998 |
| RU | 2312059 C1 | 12/2007 |
| RU | 2403379 C1 | 11/2010 |
| SU | 1498908 A1 | 8/1989 |
| SU | 1776298 | 11/1992 |
| WO | WO-2008031488 A1 | 3/2008 |
| WO | WO-2008035776 A1 | 3/2008 |
| WO | WO-2009098375 A1 | 8/2009 |

OTHER PUBLICATIONS

U.S. Appl. No. 13/684,987, filed Nov. 26, 2012 and titled Chemical Processes and Reactors for Efficiently Producing Hydrogen Fuels and Structural Materials, and Associated Systems and Methods.

U.S. Appl. No. 13/026,996, filed Feb. 14, 2011, and titled Reactor Vessels With Transmissive Surfaces for Producing Hydrogen-Based Fuels and Structural Elements, and Associated Systems and Methods.

U.S. Appl. No. 13/027,015, filed Feb. 14, 2011, and titled Chemical Reactors With Re-Radiating Surfaces and Associated Systems and Methods.

U.S. Appl. No. 13/027,244, filed Feb. 14, 2011, and titled Thermal Transfer Device and Associated Systems and Methods.

U.S. Appl. No. 13/026,990, filed Feb. 11, 2011, now U.S. Patent No. 8,187,549, issued May 29, 2012, titled Chemical Reactors With Annularly Positioned Delivery and Removal Devices, and Associated Systems and Methods.

U.S. Appl. No. 13/027,181, filed Feb. 11, 2011, now U.S. Patent No. 8,187,500, issued May 29, 2012, titled Reactors for Conducting Thermochemical Processes With Solar Heat Input, and Associated Systems and Methods.

U.S. Appl. No. 13/481,673, filed May 25, 2012, and titled Reactors for Conducting Thermochemical Processes With Solar Heat Input, and Associated Systems and Methods.

U.S. Appl. No. 13/584,748, filed Aug. 13, 2012, and titled Fuel-Cell Systems Operable in Multiple Modes for Variable Processing of Feedstock Materials and Associated Devices, Systems, and Methods.

U.S. Appl. No. 13/764,346, filed Feb. 11, 2011 and titled Fuel-Cell Systems Operable in Multiple Modes for Variable Processing of Feedstock Materials and Associated Devices, Systems, and Methods.

U.S. Appl. No. 13/027,215, filed Feb. 14, 2011, now U.S. Patent 8,318,269, issued Nov. 27, 2012 and titled Induction for Thermochemical Processes, and Associated Systems, and Methods.

U.S. Appl. No. 13/685,075, filed Nov. 26, 2012, and titled Induction for Thermochemical Process, and Associated Systems and Methods.

U.S. Appl. No. 13/584,741, filed Aug. 13, 2012, and titled Systems and Methods for Collecting and Processing PermaFrost Gases, and for Cooling PermaFrost.

U.S. Appl. No. 13/764,063, filed Feb. 11, 2013 and titled Systems and Methods for Collecting and Processing PermaFrost Gases, and for Cooling PermaFrost.

U.S. Appl. No. 13/584,688, filed Aug. 13, 2012, and titled Geothermal Energization of a Non-Combustion Chemical Reactor and Associated Systems and Methods.

U.S. Appl. No. 13/764,107, filed Feb. 11, 2013, and titled Geothermal Energization of a Non-Combustion Chemical Reactor and Associated Systems and Methods.

U.S. Appl. No. 13/027,198, filed Feb. 14, 2011, and titled Coupled Thermochemical Reactors and Engines, and Associated Systems and Methods.

U.S. Appl. No. 13/584,773, filed Aug. 13, 2012, and titled Systems and Methods for Providing Supplemental Aqueous Thermal Energy.

U.S. Appl. No. 13/764,141, filed Feb. 11, 2013, and titled Systems and Methods for Providing Supplemental Aqueous Thermal Energy.

U.S. Appl. No. 13/584,708, filed Aug. 13, 2012, and titled Systems and Methods for Extracting and Processing Gases From Submerged Sources.

U.S. Appl. No. 13/584,749, filed Aug. 13, 2012, and titled Mobile Transport Platforms for Producing Hydrogen and Structural Materials, and Associated Systems and Methods.

U.S. Appl. No. 13/584,786, filed Aug. 13, 2012, and titled Reducing and/or Harvesting Drag Energy From Transport Vehicles, Including for Reactors, and Associated Systems and Methods.

U.S. Appl. No. 13/764,493, filed Feb. 11, 2013, and titled Reducing and/or Harvesting Drag Energy From Transport Vehicles, Including for Chemical Reactors, and Associated Systems and Methods.

U.S. Appl. No. 13/027,060, filed Feb. 14, 2011, now U.S. Patent No. 8,318,100, issued Nov. 27, 2012 and titled Reactor Vessels With Pressure and Heat Transfer Features for Producing Hydrogen-Based Fuels and Structural Elements, and Associated Systems and Methods.

U.S. Appl. No. 13/684,743, filed Nov. 26, 2012, and titled Reactor Vessels With Pressure and Heat Transfer Features for Producing Hydrogen-Based Fuels and Structural Elements, and Associated Systems and Methods.

U.S. Appl. No. 13/832,740, filed Mar. 15, 2013, and titled Engine Exhaust Manifold Endothermic Reactor and Associated Systems and Methods.

"Carnot Thermochemical Cycles." Digital image. Wikipedia, the Free Encyclopedia, Published: Aug. 31, 2010. Accessed: Jan. 4, 2011. Printed: May 20, 2011. <http://en.wikipedia.org/wiki/File:Carnot_thermochemical_cycles.PNG>. p. 1.

"Closed Loop Thermochemical Energy Storage System Using Ammonia." Australian National University College of Engineering & Computer Science—Solar Thermal Group. Accessed: Jan. 4, 2011. Printed: May 20, 2011. <http://solar-thermal.anu.edu.au/high-temperature/thermochemical-energy-storage/>. pp. 1-2.

"Si Cycle." Digital image. Sandia National Laboratories: Energy, Resources and Nonproliferation. Accessed: Jan. 4, 2011. Printed: Jun. 13, 2011. <http://www.sandia.gov/ERN/images/Si-cycle2.jpg>. p. 1.

"Solar Hydrogen." Digital image. Swiss Federal Institute of Technology, Department of Mechanical and Process Engineering, Zurich. Accessed: Jan. 4, 2011. Printed: May 23, 2011. p. 1. <http://www.pre.ethz.ch/research/projects/imgs/solarhydro_1.jpg>.

"The Carbon Cycle : Feature Articles." NASA Earth Observatory : Home. Web. Accessed: Jul. 1, 2010. Printed: Jun. 13, 2011. 12 Pages. <http://earthobservatory.nasa.gov/Features/CarbonCycle>.

"The Solar Zinc Route." Digital image. Swiss Federal Institute of Technology, Department of Mechanical and Process Engineering, Zurich. Accessed: Jan. 4, 2011. Printed: May 20, 2011. <http://www.pre.ethz.ch/research/projects/imgs/solzinc_1.jpg>. p. 1.

"Zinc Zinc-oxide Thermochemical Cycle." Digital image. Wikipedia, the Free Encyclopedia, Published: Dec. 21, 2008. Accessed: Jan. 4, 2011. Printed: May 20, 2011. <http://en.wikipedia.org/wiki/File:Zinc_zinc-oxide_thermochemical_cycle.jpg>. p. 1.

Chen et al. "Thermochemistry Concept Map." Teacherknowledge Wikispace, Published: Nov. 20, 2006. <http://teacherknowledge.wikispaces.com/file/view/Thermochemistry+concept+map+-+Extended.pdf>. p. 1.

Food and Agriculture Organization of the United Nations. "Carbon Sequestration Options under the Clean Development Mechanism to Address Land Degradation." World Soil Resources Reports. Rome, 2000. pp. 1-45.

Foust et al. "An Economic and Environmental Comparison of a Biochemical and a Thermochemical Lignocellulosic Ethanol Conversion Processes." Cellulose, vol. 16, Issue 4. Jun. 10, 2009. pp. 547-565.

Funk, James E. "Thermochemical Processes for the Production of Hydrogen from Water." College of Engineering, University of Kentucky, Lexington, Kentucky. 1975. pp. 1-9.

Hackett et al. "Evaluation of Conversion Technoloigy Processes and Products: Appendix A—Discussion of Thermochemical Process Definitions." University of California, Davis. Sep. 2004. pp. 1-7.

International Search Report and Written Opinion for PCT Application No. PCT/US11/24761; Applicant: McAlister Technologies, LLC; Date of Mailing: Oct. 19, 2011; 10 pages.

Kasting, James F. "The Carbon Cycle, Climate, and the Long-Term Effects of Fossil Fuel Burning." U.S. Global Change Research Infor-

(56) References Cited

OTHER PUBLICATIONS mation Office. 1998. Web. Accessed: Jul. 1, 2010. Printed: Jun. 13, 2011. <http://www.gcrio.org/CONSEQUENCES/vol4no1/carbcycle.html>.
Solar Collectors, Energy Storage, and Materials, pp. 443-444 (DeWinter, Francis, 1991).
U.S. Energy Information Administration."Greenhouse Gases—Energy Explained, Your Guide to Understanding Energy." Web. Accessed: Jul. 1, 2010. Printed: Jun. 13, 2011. 1 Pages. <http://www.eia.gov/energyexplained/index.cfm?page=environment_about_ghg>.
US Environmental Protection Agency. "Cap and Trade." Web. Accessed: Jul. 1, 2010. Printed: Jun. 13, 2011. <http://www.epa.gov/captrade/>.
US Environmental Protection Agency. "Carbon Dioxide—Geologic Sequestration | Climate Change—Greenhouse Gas Emissions | U.S. EPA." Web. Accessed: Jul. 1, 2010. Printed: Jun. 13, 2011. <http://www.epa.gov/climatechange/emissions/co2_geosequest.html>.
US Environmental Protection Agency. "Carbon Dioxide | Climate Change—Greenhouse Gas Emissions | U.S. EPA". Web. Accessed: Jul. 1, 2010. Printed: Jun. 13, 2011. 1 Page. <http://www.epa.gov/climatechange/emissions/co2.html>.
US Environmental Protection Agency. "EPA Preliminary Analysis of the Waxman-Markey Discussion Draft". Web. Accessed: Jul. 1, 2010. Printed: Jun. 13, 2011. <http://www.epa.gov/climatechange/economics/pdfs/WM-Analysis.pdf>.
Vegners, Raimonds Maris; "Collodial Carbon and Silica : Their Use in Solar Energy" Table of Contents and Introduction of Thesis, University of Sydney, Feb. 1985, 5 pages.
Wikipedia > Aerogel > Carbon—"Carbon aerogels are also extremely 'black' in the infrared spectrum, reflecting only 0.3% of radiation behven 250 nm and 14.3 µm, making them efficient for solar energy collectors," 1 page.

\* cited by examiner

CHEMICAL REACTORS WITH ANNULARLY POSITIONED DELIVERY AND REMOVAL DEVICES, AND ASSOCIATED SYSTEMS AND METHODS

CROSS-REFERENCE TO RELATED APPLICATIONS

The present application is a Continuation of U.S. patent application No. 13/026,990 filed Feb. 14, 2011, now U.S. Pat. No. 8,187,549 issued May 24, 2012 and titled CHEMICAL REACTORS WITH ANNULARLY POSITIONED DELIVERY AND REMOVEAL DEVICES, AND ASSOCIATED SYSTEMS AND METHODS, which application claims priority to and the benefit of U.S. patent application Ser. No. 61/304,403, filed on Feb. 13, 2010 and titled FULL SPECTRUM ENERGY AND RESOURCE INDEPENDENCE, which is incorporated herein by reference in its entirety. To the extent the foregoing application and/or any other materials incorporated herein by reference conflict with the disclosure presented herein, the disclosure herein controls.

TECHNICAL FIELD

The present technology relates generally to chemical reactors with annularly positioned reactant delivery devices and product removal devices, and associated systems and methods. In particular embodiments, reactor systems with these devices can be used to produce clean-burning, hydrogen-based fuels from a wide variety of feedstocks with enhanced energy efficiency, and can produce structural building blocks from carbon and/or other elements that are released when forming the hydrogen-based fuels.

BACKGROUND

Renewable energy sources such as solar, wind, wave, falling water, and biomass-based sources have tremendous potential as significant energy sources, but currently suffer from a variety of problems that prohibit widespread adoption. For example, using renewable energy sources in the production of electricity is dependent on the availability of the sources, which can be intermittent. Solar energy is limited by the sun's availability (i.e., daytime only), wind energy is limited by the variability of wind, falling water energy is limited by droughts, and biomass energy is limited by seasonal variances, among other things. As a result of these and other factors, much of the energy from renewable sources, captured or not captured, tends to be wasted.

The foregoing inefficiencies associated with capturing and saving energy limit the growth of renewable energy sources into viable energy providers for many regions of the world, because they often lead to high costs of producing energy. Thus, the world continues to rely on oil and other fossil fuels as major energy sources because, at least in part, government subsidies and other programs supporting technology developments associated with fossil fuels make it deceptively convenient and seemingly inexpensive to use such fuels. At the same time, the replacement cost for the expended resources, and the costs of environment degradation, health impacts, and other by-products of fossil fuel use are not included in the purchase price of the energy resulting from these fuels.

In light of the foregoing and other drawbacks currently associated with sustainably producing renewable resources, there remains a need for improving the efficiencies and commercial viabilities of producing products and fuels with such resources.

DETAILED DESCRIPTION

1. Overview

Figure 1:
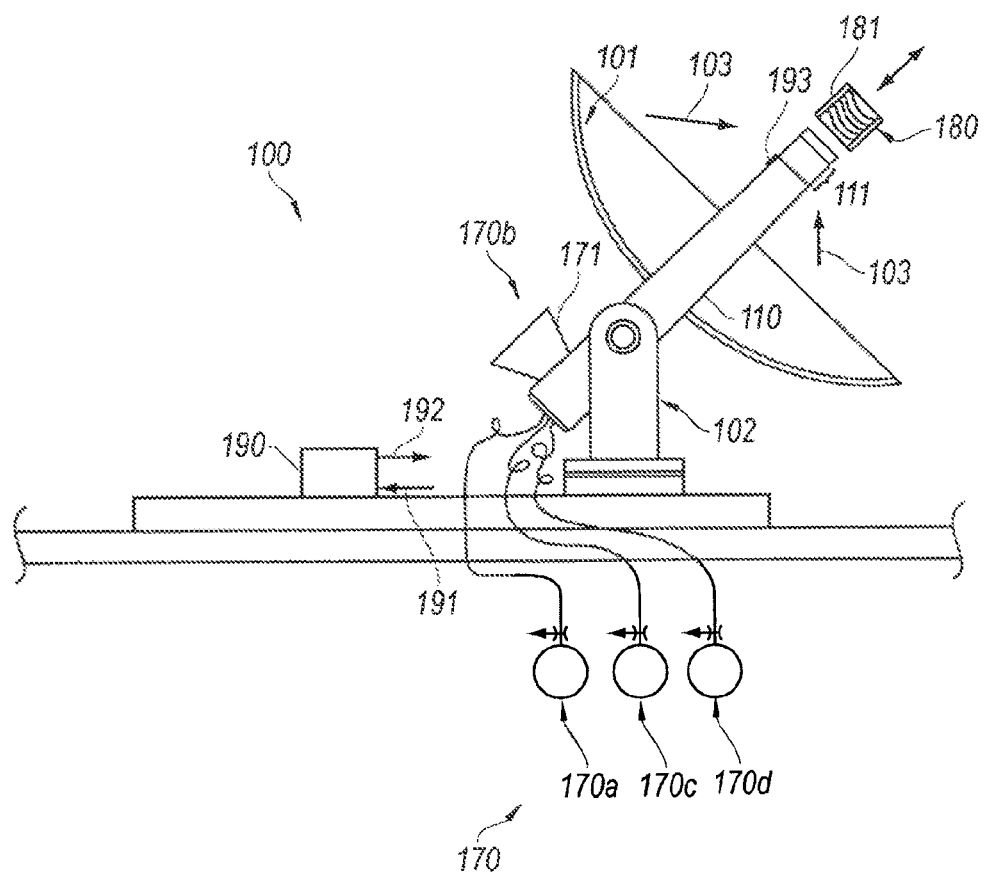
FIG. 1 is a partially schematic illustration of a system having a solar concentrator that directs heat to a reactor vessel in accordance with an embodiment of the disclosed technology.

Several examples of devices, systems and methods for handling reactants and products in a chemical reactor are described below. In particular embodiments, these devices can improve the efficiency with which reactants are compacted and heated so as to improve the overall efficiency of the reaction. Reactors that include these devices can be used to produce hydrogen fuels and/or other useful end products from biomass and/or other waste streams. Accordingly, the reactors can produce clean-burning fuel and can re-purpose carbon and/or other constituents for use in durable goods, including polymers and carbon composites. Although the following description provides many specific details of the following examples in a manner sufficient to enable a person skilled in the relevant art to practice, make and use them, several of the details and advantages described below may not be necessary to practice certain examples of the technology. Additionally, the technology may include other examples that are within the scope of the claims but are not described here in detail.

References throughout this specification to "one example," "an example," "one embodiment" or "an embodiment" mean that a particular feature, structure, process or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include internet appliances, hand-held devices, multi-processor systems, programmable consumer electronics, network computers, mini-computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well as media distributed electronically over networks. In particular embodiments, data structures and transmissions of data particular to aspects of the technology are also encompassed within the scope of the present technology. The present technology encompasses both methods of programming computer-readable media to perform particular steps, as well as executing the steps.

A chemical reactor in accordance with a particular embodiment includes a reactor vessel having a light-transmissible surface proximate to a reaction zone. The reactor can further include a movable reactant delivery system positioned within the reactor vessel, and a product removal system positioned within the vessel and positioned annularly inwardly or outwardly from the delivery system. The solar concentrator is positioned to direct solar radiation through the light-transmissible surface to the reaction zone. The annular relationship between the reactant delivery system and product withdrawal system can enhance heat transfer between outgoing products and incoming reactants, and can facilitate compressing the incoming reactants prior to entering the reactor.

A method in accordance with a particular embodiment of the technology includes concentrating solar radiation and directing the concentrated solar radiation through a light-transmissive surface of a reaction vessel and to a reaction zone within the reaction vessel. A reactant delivery system is actuated to direct a reactant to the reaction zone. The method can further include performing an endothermic reaction at the reaction zone to produce a product, and actuating a product removal system position annularly inwardly or outwardly from the reactant delivery system to remove a product from the reaction zone.

2. Representative Reactors and Associated Methodologies

FIG. 1 is a partially schematic illustration of a system 100 including a reactor vessel 110 having a reaction zone 111. The system 100 further includes a solar collector 101 that directs solar energy 103 to the reaction zone 111. The solar collector 103 can include a dish, trough, heliostat arrangement, fresnel lens and/or other radiation-focusing element. The reactor vessel 110 and the solar collector 101 can be mounted to a pedestal 102 that allows the solar collector 101 to rotate about at least two orthogonal axes in order to continue efficiently focusing the solar energy 103 as the earth rotates. The system 100 can further include multiple reactant/product vessels 170, including first and second reactant vessels 170a, 170b, and first and second product vessels, 170c, 170d. In particular embodiments, the first reactant vessel 170a can provide a reactant that contains hydrogen and carbon, such as methane, which is processed at the reaction zone 111 in an endothermic reaction to produce hydrogen and carbon which is provided to the first and second product vessels 170c, 170d, respectively.

In other embodiments, other reactants, for example, municipal solid waste streams, biomass reactants, and/or other waste streams can be provided at a hopper 171 forming a portion of the second reactant vessel 170b. In any of these embodiments, an internal reactant delivery system and product removal system provide the reactants to the reaction zone 111 and remove the products from the reaction zone 111, as will be described in further detail later with reference to FIGS. 3-6.

The system 100 can further include a supplemental heat source 180 that provides heat to the reaction zone 111 when the available solar energy 103 is insufficient to sustain the endothermic reaction at the reaction zone 111. In a particular embodiment, the supplemental heat source 180 can include an inductive heater 181 that is positioned away from the reaction zone 111 during the day to allow the concentrated solar energy 103 to enter the reaction zone 111, and can slide over the reaction zone 111 at night to provide heat to the reaction zone 111. The inductive heater 181 can be powered by a renewable clean energy source, for example, hydrogen produced by the reactor vessel 110 during the day, or falling water, geothermal energy, wind energy, or other suitable sources.

In any of the foregoing embodiments, the system 100 can further include a controller 190 that receives input signals 191 and directs the operation of the devices making up the system 100 via control signals or other outputs 192. For example, the controller 190 can receive a signal from a radiation sensor 193 indicating when the incident solar radiation is insufficient to sustain the reaction at the reaction zone 111. In response, the controller 190 can issue a command to activate the supplemental heat source 180. The controller 190 can also direct the reactant delivery and product removal systems, described further below with reference to FIGS. 3-6.

Figure 2:
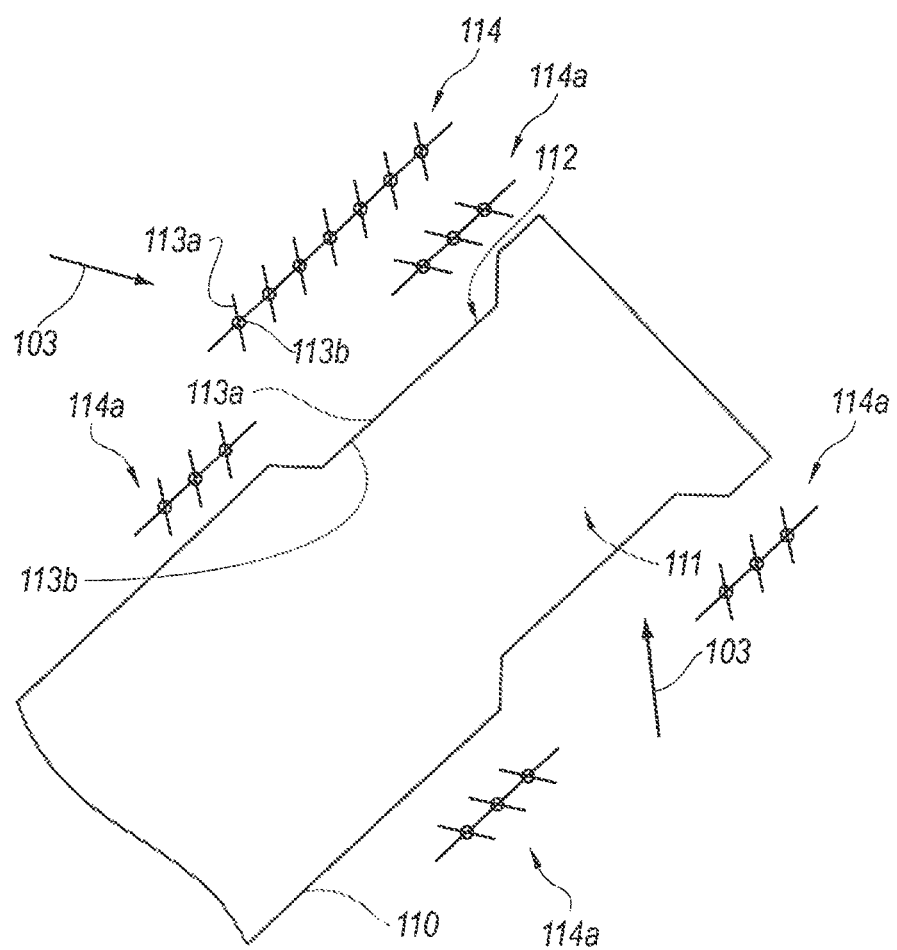
FIG. 2 is a partially schematic, enlarged illustration of a portion of a reactor vessel, including additional features for controlling the delivery of solar energy to the reaction zone in accordance with an embodiment of the disclosed technology.

FIG. 2 is a partially schematic illustration of an embodiment of the reactor vessel 110 shown in FIG. 1, illustrating a transmissive component 112 positioned to allow the incident solar energy 103 to enter the reaction zone 111. In a particular embodiment, the transmissive component 112 can include a glass or other suitably transparent, high temperature material that is easily transmissible to solar radiation, and configured to withstand the high temperatures in the reaction zone 111. For example, temperatures at the reaction zone 111 are in some embodiments expected to reach 4000° F., and can be higher for the reactants and/or products.

In other embodiments, the transmissive component 112 can include one or more elements that absorb radiation at one wavelength and re-radiate it at another. For example, the transmissive component 112 can include a first surface 113a that receives incident solar energy at one wavelength and a second surface 113b that re-radiates the energy at another wavelength into the reaction zone 111. In this manner, the energy provided to the reaction zone 111 can be specifically tailored to match or approximate the absorption characteristics of the reactants and/or products placed within the reaction zone 111, Further details of representative re-radiation devices are described in co-pending U.S. Application No. 13/027,015 titled, "CHEMICAL REACTORS WITH RE-RADIATING SURFACES AND ASSOCIATED SYSTEMS AND METHODS" filed concurrently herewith and incorporated herein by reference.

In other embodiments, the reactor vessel 110 can include other structures that perform related functions, For example, the reactor vessel 110 can include a Venetian blind arrangement 114 having first and second surfaces 113a, 113b that can be pivoted to present one surface or the other depending upon external conditions, e.g., the level of incident solar energy 103, hi a particular aspect of this embodiment, the first surface 113a can have a relatively high absorptivity and a relatively low emissivity, This surface can accordingly readily absorb radiation during the day. The second surface 113b can have a relatively low absorptivity and a relatively high emissivity and can accordingly operate to cool the reaction zone 111 (or another component of the reactor 110), e.g., at night. A representative application of this arrangement is a reactor that conducts both endothermic and exothermic reactions, as is described further in co-pending U.S. Application No. 13/027,060 titled "REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS". Further details of other arrangements for operating the solar collector 101 (FIG. 1) in a cooling mode are described in co-pending U.S. Application No. 13/027,181 titled "REACTORS FOR CONDUCTING THERMOCHEMICAL PROCESSES WITH SOLAR HEAT INPUT, AND ASSOCIATED SYSTEMS AND METHODS", filed concurrently herewith and incorporated herein by reference.

In still further embodiments, the reactor 110 can include features that redirect radiation that "spills" (e.g., is not precisely focused on the transmissive component 112) due to collector surface aberrations, environmental defects, non-parallel radiation, wind and/or other disturbances or distortions. These features can include additional Venetian blinds 114a that can be positioned and/or adjusted to redirect radiation (with or without wavelength shifting) into the reaction zone 111.

Figure 3:
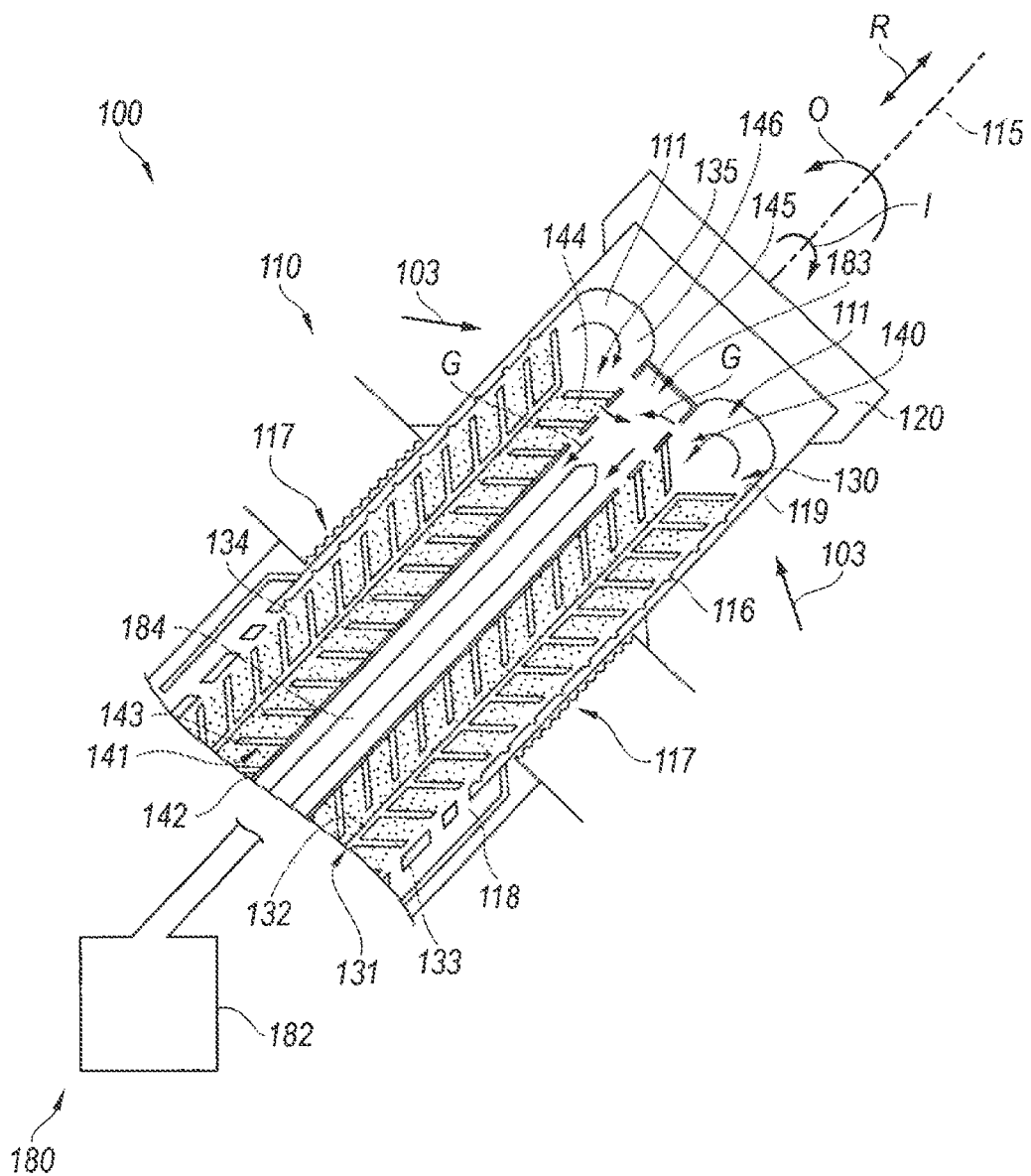
FIG. 3 is a partially schematic, cross-sectional illustration of an embodiment of a reactor vessel having annularly positioned product removal and reactant delivery systems in accordance with an embodiment of the disclosure.

FIG. 3 is a partially schematic, cross-sectional illustration of a portion of a reactor vessel 110 configured in accordance with an embodiment of the present disclosure. In one aspect of this embodiment, the reactor 110 includes a reactant delivery system 130 that is positioned within a generally cylindrical, barrel-shaped reactor vessel 110, and a product removal system 140 positioned annularly inwardly from the reactant delivery system 130. For example, the reactant delivery system 130 can include an outer screw 131, which in turn includes an outer screw shaft 132 and outwardly extending outer screw threads 133. The outer screw 131 has an axially extending first axial opening 135 in which the product removal system 140 is positioned. The outer screw 131 rotates about a central rotation axis 115, as indicated by arrow O. As it does so, it carries at least one reactant 134 (e.g., a gaseous, liquid, and/or solid reactant) upwardly and to the right as shown in FIG. 3, toward the reaction zone 111. As the reactant 134 is carried within the outer screw threads 133, it is also compacted, potentially releasing gases and/or liquids, which can escape through louvers and/or other openings 118 located annularly outwardly from the outer screw 131. As the reactant 134 becomes compacted in the outer screw threads 133, it forms a seal against an inner wall 119 of the vessel 110. This arrangement can prevent losing the reactant 134, and can instead force the reactant 134 to move toward the reaction zone 111. The reactant delivery system 130 can include other features, in addition to the outer screw threads 133, to force the reactant 134 toward the reaction zone 111. For example, the inner wall 119 of the reactor vessel 110 can include one or more spiral rifle grooves 116 that tend to force the reactant 134 axially as the outer screw 131 rotates. In addition to, or in lieu of this feature, the entire outer screw 131 can reciprocate back and forth, as indicated by arrow R to prevent the reactant 134 from sticking to the inner wall 119, and/or to release reactant 134 that may stick to the inner wall 119. A barrel heater 117 placed near the inner wall 119 can also reduce reactant sticking, in addition to or in lieu of the foregoing features. In a least some embodiments, it is expected that the reactant 134 will be less likely to stick when warn The reactant 134 can include a variety of suitable compositions, e.g., compositions that provide a hydrogen donor to the reaction zone 111. In representative embodiments, the reactant 134 can include biomass constituents, e.g., municipal solid waste, commercial waste, forest product waste or slash, cellulose, lignocellulose, hydrocarbon waste (e.g., tires), and/or others. After being compacted, these waste products can be highly subdivided, meaning that they can readily absorb incident radiation due to rough surface features and/or surface features that re-reflect and ultimately absorb incident radiation. This property can further improve the efficiency with which the reactant 134 heats up in the reaction zone 111.

Once the reactant 134 has been delivered to the reaction zone 111, it receives heat from the incident solar energy 103 or another source, and undergoes an endothermic reaction. The reaction zone 111 can have an annular shape and can include insulation 120 to prevent heat from escaping from the vessel 110. In one embodiment, the endothermic reaction taking place at the reaction zone 111 includes dissociating methane, and reforming the carbon and hydrogen constituents into elemental carbon and diatomic hydrogen, or other carbon compounds (e.g., oxygenated carbon in the form of carbon monoxide or carbon dioxide) and hydrogen compounds. The resulting product 146 can include gaseous portions (indicated by arrow G), which passed annularly inwardly from the reaction zone 111 to be collected by the product removal system 140, Solid portions 144 (e.g., ash and/or other byproducts) of the product 146 are also collected by the product removal system 140.

The product removal system 140 can include an inner screw 141 positioned in the first axial opening 135 within the outer screw 131. The inner screw 141 can include an inner screw shaft 142 and inner screw threads 143. The inner screw 141 can also rotate about the rotation axis 115, as indicated by arrow I, in the same direction as the outer screw 131 or in the opposite direction. The inner screw 141 includes a second axial passage 145 having openings that allow the gaseous product G to enter. The gaseous product G travels down the second axial opening 145 to be collected and, in at least some instances, further processed (e.g., to isolate the carbon produced in the reaction from the hydrogen produced in the reaction). In particular embodiments, the gaseous product C can exchange additional heat with the incoming reactant 134 via an additional heat exchanger (not shown in FIG. 3) to cool the product C and heat the reactant 134. hi other embodiments, the gaseous product C can be cooled by driving a Stirling engine or other device to generate mechanical and/or electric power. As the inner screw 141 rotates, it carries the solid portions 144 of the product 146 downwardly and to the left as shown in FIG. 3. The sold products 144 (and the gaseous product C) can convey heat via conduction to the outer screw 130 to heat the incoming reactant 134, after which the sold portions 144 can be removed for use. For example, nitrogenous and/or sulfurous products from the reaction performed at the reaction zone 111 can be used in agricultural or industrial processes. The products and therefore the chemical and physical composition of the sold portions can depend on the characteristics of the incoming reactants, which can vary widely, e.g., from municipal sold waste to industrial waste to biomass.

As discussed above with reference to FIGS. 1 and 2, the system 100 can include features that direct energy (e.g., heat) into the reaction zone 111 even when the available solar energy is insufficient to sustain the reaction, in an embodiment shown in FIG. 3, the supplemental heat source 180 can include combustion reactants 182 (e.g., an oxidizer and/or a hydrogen-containing combustible material) that is directed through a delivery tube 184 positioned in the second axial opening 145 to a combustor or combustor zone 183 that is in thermal communication with the reaction zone 111. During the night or other periods of time when the incident solar energy is low, the supplemental heat source 180 can provide additional heat to the reaction zone 111 to sustain the endothermic reaction taking place therein.

One feature of an embodiment described above with reference to FIG. 3 is that the incoming reactant 134 can be in close or intimate thermal communication with the solid product 144 leaving the reaction zone. In particular, the outer screw shaft 132 and outer screw threads 133 can be formed from a highly thermally conductive material, so as to receive heat from the solid product 144 carried by the inner screw 141, and deliver the heat to the incoming reactant 134. An advantage of this arrangement is that it is thermally efficient because it removes heat from products that would otherwise be cooled in a manner that wastes the heat, and at the same time heats the incoming reactants 134, thus reducing the amount of heat that must be produced by the solar concentrator 101 (FIG. 1) and/or the supplemental heat source 180. By improving the efficiency with which hydrogen and/or carbon or other building blocks are produced in the reactor vessel 110, the reactor system 100 can increase the commercial viability of the renewable reactants and energy sources used to produce the products.

Figure 4:
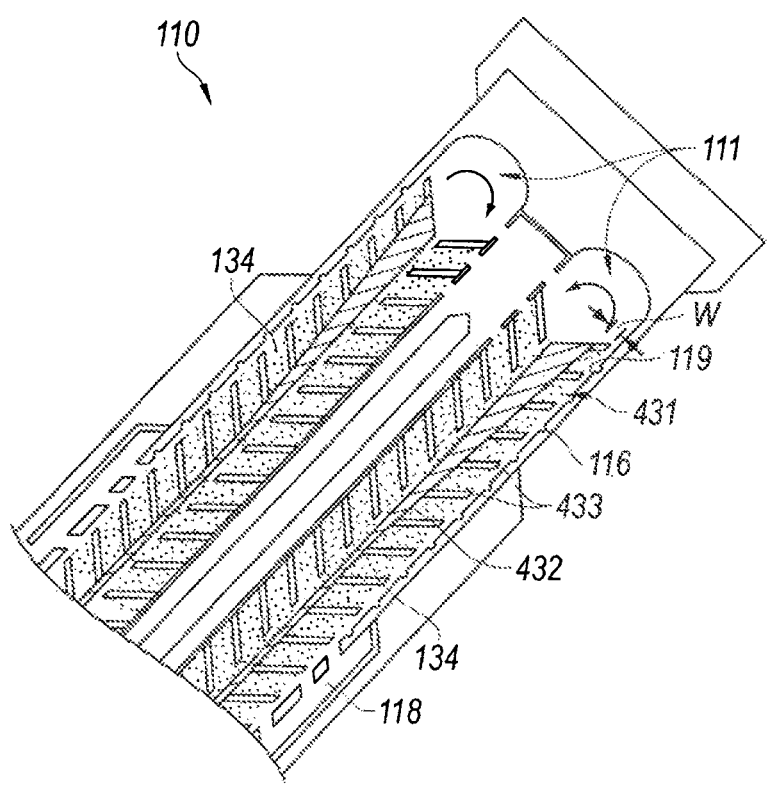
FIG. 4 is a partially schematic, cross-sectional illustration of a reactant delivery system having radially tapered screw threads in accordance with an embodiment of the disclosed technology.

FIG. 4 is a partially schematic, cross-sectional illustration of an embodiment of the reactor vessel 110 having an outer screw 431 particularly configured to compact the reactant 134 that it carries. In this embodiment, the outer screw 431 includes a screw shaft 432 that tapers outwardly, thus reducing the radial width W of the screw threads 433 in an axial direction toward the reaction zone 111. This arrangement effectively reduces the volume between neighboring screw threads 433 in a direction toward the reaction zone 111, thus compacting the reactant 134. Over at least one portion of its length, the outer screw 431 can effectively remove air and moisture from the reactant 134, allowing the air and moisture to be withdrawn through the openings/louvers 118. These constituents might otherwise slow the rate of reaction at the reaction zone 111. As the reactant 134 is further compacted, it also seals against the inner wall 119 of the reactor vessel 110 to prevent liquids and gases from escaping when they might otherwise participate in the reaction at the reaction zone 111. The heat produced when compacting the reactant 134 can reduce the amount of energy required to be produced by the solar concentrator 101 (FIG. 1) or other energy source.

Figure 5:
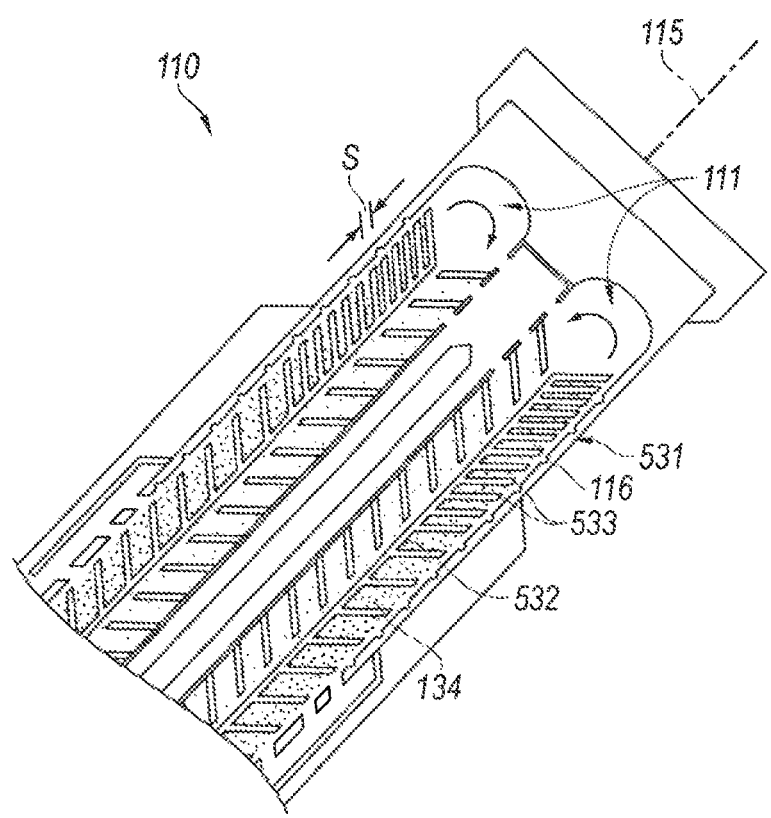
FIG. 5 is a partially schematic, cross-sectional illustration of a reactor vessel having a reactant delivery system with screw thread channels that narrow in an axial direction in accordance with an embodiment of the disclosed technology.

In other embodiments, other mechanisms and devices can be used to compact the reactant 134 as it is directed to the reaction zone 111. For example, FIG. 5 illustrates a reactor vessel 110 having an outer screw 531 with a shaft 532 carrying screw threads 533 that have a closer or smaller axial spacing (indicated by gap S) the closer the threads 533 are to the reaction zone 111. Accordingly, the pitch of the screw threads 533 can gradually decrease in an axial direction along the rotation axis 115. In any of the foregoing embodiments, the volume between neighboring threads is smaller proximate to the reaction zone 111 than it is distal from the reaction zone 111.

Figure 6:
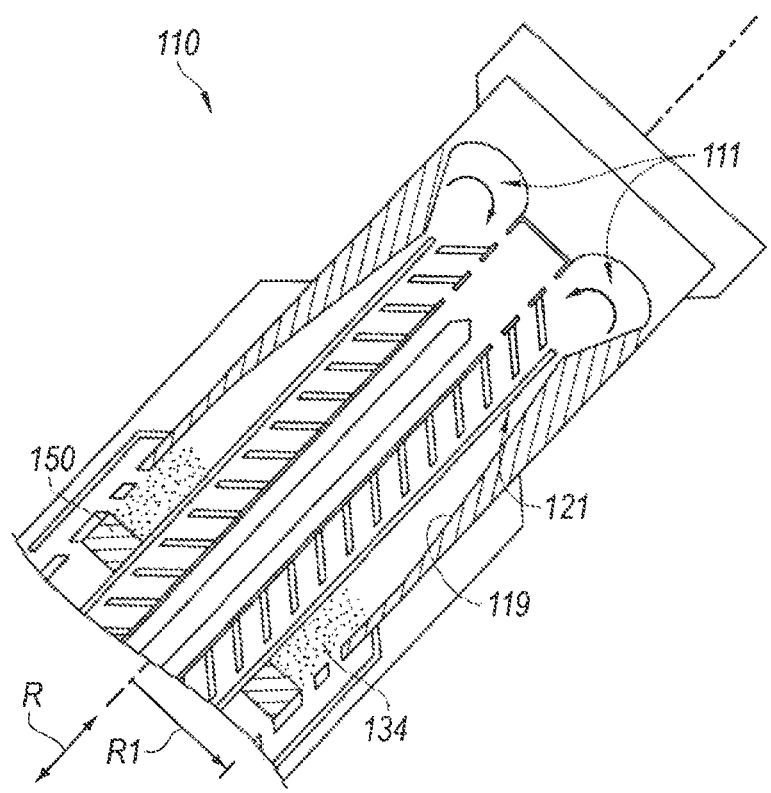
FIG. 6 is a partially schematic, cross-sectional illustration of a reactor vessel having a reactant delivery system that includes an annularly positioned piston within a cylinder having tapered walls, in accordance with yet another embodiment of the disclosed technology.

In the embodiments described above with reference to FIGS. 3-5, the reactant 134 is delivered and compacted by a spiral screw. In other embodiments, the reactant 134 can be delivered and compacted via other mechanisms, for example, a piston. FIG. 6 is a partially schematic, cross-sectional illustration of the reactor vessel 110 in which the reactant 134 is loaded on or ahead of a ring-shaped piston 150 that moves back and forth as indicated by arrow R within the reactor vessel 110. After the loading operation, the piston 150 drives toward the reaction zone 111, thus compacting the reactant 134 against an inwardly tapering vessel inner wall 119, which forms a tapered channel 121.

In one mode of operation, the piston 150 drives the reactant 134 against the tapered vessel inner wall 119, and then is withdrawn to allow more reactant to be placed in the reactor vessel 110. The additional reactant 134 is then driven against the reactant 134 already present between the vessel inner walls 119, thus forcing the reactant 134 entirely through the tapered channel 121 and into the reaction zone 111. This process can be repeated to deliver the reactant 134 to the reaction zone 111 in a series of pulses or steps.

In another mode of operation, the piston 150 can be formed from a material that collapses or compresses in a radial direction R1, thus allowing the piston 150 to drive entirely through the tapered channel 121 to deliver the entire amount of reactant 134 within the tapered channel 121 in one stroke. In other embodiments, the reactor 110 can include other arrangements for compacting the incoming reactant 134, while allowing the hot, exiting product to preheat the reactant 134 and thus reduce the amount of thermal energy that must be provided at the reaction zone 111 via solar or other sources to sustain an endothermic reaction.

From the foregoing, it will be appreciated that specific embodiments of the technology have been described herein for purposes of illustration, but that various modifications may be made without deviating from the technology. For example, reactions at the reaction zone 111 can be conducted on reactants other then methane. Such reactants can include other hydrocarbons, or other hydrogen donors that do not include carbon. Such hydrogen donors can include nitrogenous donors, and/or donors that include boron, silicon, or sulfur. Nitrogenous donors can include biomass constituents and/or other constituents. The solar collector can have a dish shaped arrangement, as shown in FIG. 1, or other arrangements (e.g., a trough shape or a heliostat arrangement) in other embodiments. Embodiments of the supplemental heat source described above were described in the context of an inductive heater and a combustor. In other embodiments, the supplemental heat source can include other devices that provide energy to the reaction zone 111 Reactors in accordance with still further embodiments do not receive heat from solar energy and accordingly can rely on what (in some embodiments described above) is considered a supplemental heat source, as a primary heat source.

Certain aspects of the technology described in the context of particular embodiments may be combined or eliminated in other embodiments. For example, the outer screw can include both a tapered screw shaft and varying spacing between adjacent threads to compact the reactant 134. In particular embodiments, the outer screw carries the reactant and the inner screw carries the solid products. In other embodiments, the roles of the inner and outer screws can be reversed. The arrangement described above with reference to FIG. 6 identified a piston positioned annularly outwardly from an inner threaded shaft. In other embodiments, an additional piston can replace the inner threaded shaft, or an inner piston can be used in conjunction with an outer threaded shaft. Further, while advantages associated with certain embodiments of the technology have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

To the extent not previously incorporated herein by reference, the present application incorporates by reference in their entirety the subject matter of each of the following materials: U.S. patent application Ser. No. 12/857,553, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,553, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010 and titled ENERGY SYSTEM FOR DWELLING SUPPORT; filed on Feb. 14, 2011 and titled DELIVERY SYSTEMS WITH IN-LINE SELECTIVE EXTRACTION DEVICES AND ASSOCIATED METHODS OF OPERATION; U.S. patent application Ser. No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; filed on Feb. 14, 2011 and titled CHEMICAL REACTORS WITH RE-RADIATING SURFACES AND ASSOCIATED SYSTEMS AND METHODS; filed on Feb. 14, 2011 and titled THERMAL TRANSFER DEVICE AND ASSOCIATED SYSTEMS AND METHODS; filed on Feb. 14, 2011 and titled REACTORS FOR CONDUCTING THERMOCHEMICAL PROCESSES WITH SOLAR HEAT INPUT, AND ASSOCIATED SYSTEMS AND METHODS; filed on Feb. 14, 2011 and titled INDUCTION FOR THERMOCHEMICAL PROCESS, AND ASSOCIATED SYSTEMS AND METHODS; filed on Feb. 14, 2011 and titled COUPLED THERMOCHEMICAL REACTORS AND ENGINES, AND ASSOCIATED SYSTEMS AND METHODS; U.S. Patent Application Ser. No. 61/385,508, filed on Sep. 22, 2010 and titled REDUCING AND HARVESTING DRAG ENERGY ON MOBILE ENGINES USING THERMAL CHEMICAL REGENERATION; filed on Feb. 14, 2011 and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; filed on Feb. 14, 2011 and titled ARCHITECTURAL CONSTRUCT HAVING FOR EXAMPLE A PLURALITY OF ARCHITECTURAL CRYSTALS; U.S. patent application Ser. No. 12/806,634, filed on Aug. 16, 2010 and titled METHODS AND APPARATUSES FOR DETECTION OF PROPERTIES OF FLUID CONVEYANCE SYSTEMS; filed on Feb. 14, 2011 and titled METHODS, DEVICES, AND SYSTEMS FOR DETECTING PROPERTIES OF TARGET SAMPLES; filed on Feb. 14, 2011 and titled SYSTEM FOR PROCESSING BIOMASS INTO HYDROCARBONS, ALCOHOL VAPORS, HYDROGEN, CARBON, ETC.; filed on Feb. 14, 2011 and titled CARBON RECYCLING AND REINVESTMENT USING THERMOCHEMICAL REGENERATION; filed on Feb. 14, 2011 and titled OXYGENATED FUEL; U.S. Patent Application Ser. No. 61/237419, filed on Aug. 27, 2009 and titled CARBON SEQUESTRATION; U.S. Patent Application Ser. No. 61/237425, filed on Aug. 27, 2009 and titled OXYGENATED FUEL PRODUCTION; filed on Feb. 14, 2011 and titled MULTI-PURPOSE RENEWABLE FUEL FOR ISOLATING CONTAMINANTS AND STORING ENERGY; U.S. Patent Application Ser. No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; filed on Feb. 14, 2011 and titled ENGINEERED FUEL STORAGE, RESPECIATION AND TRANSPORT;

I claim:

1. A method for performing a chemical reaction, comprising:
concentrating solar radiation;
directing the concentrated solar radiation through a light-transmissive surface of a reaction vessel and to a reaction zone within the reaction vessel;
actuating a reactant delivery system to direct a reactant to the reaction zone;
performing an endothermic reaction at the reaction zone to produce a product; and
actuating a product removal system positioned annularly inwardly or outwardly from the reactant delivery system to remove a product from the reaction zone while transferring heat from the product radially outwardly or inwardly to a reactant volume carried by the reactant delivery system.

2. The method of claim 1, further comprising compacting the reactant as the reactant approaches the reaction zone.

3. The method of claim 1 wherein the reactant includes at least one solid reactant.

4. The method of claim 1 wherein the reactant includes at least one gaseous reactant.

5. The method of claim 1 wherein the reactant includes a biomass reactant, and wherein compacting the reactant includes removing water and air from the reactant.

6. A method for performing a chemical reaction, comprising:
concentrating solar radiation during daylight hours;
directing the concentrated solar radiation through a light-transmissive surface of a reaction vessel and to a reaction zone within the reaction vessel;
rotating a first helical screw to direct a hydrocarbon reactant to the reaction zone;
performing an endothermic reaction at the reaction zone to dissociate the hydrocarbon into a gaseous hydrogen-containing constituent and a gaseous carbon-containing constituent and the gaseous carbon-containing constituent from the reaction zone;
rotating a second helical screw located within an axial aperture of the first helical screw to remove the solid product from the reaction zone;
after daylight hours, directing oxygen to the reaction zone via a gas conduit located within an axial aperture of the first helical screw to support a combustion process; and
directing heat from the combustion process to the reaction zone.

7. The method of claim 6, further comprising transferring heat from the source products to an incoming hydrocarbon reactant as at least one of the first and second helical screws rotates relative to the other.

8. The method of claim 1 wherein directing a reactant includes directing a hydrocarbon reactant.

9. The method of claim 1 wherein directing a reactant includes directing a nitrogen-bearing reactant.

10. The method of claim 1 wherein directing a reactant includes directing a biomass reactant.

11. The method of claim 1 wherein removing a product includes removing a hydrogen-bearing product.

12. The method of claim 1 wherein conducting a reaction includes conducting a dissociation reaction.

13. The method of claim 1, further comprising supplementing the concentrated solar radiation with heat from a supplemental heat source.

14. The method of claim 13, further comprising sliding the supplemental heat source over the reaction zone.

15. The method of claim 13 wherein the supplemental heat source includes an inductive heat source.

16. The method of claim 1 wherein the product removal system is positioned annularly inwardly from the reactant delivery system.

17. The method of claim 1 wherein actuating the product removal system includes rotatating a screw having an outwardly-extending helical thread positioned to convey the products from the reaction zone.

18. The method of claim 1 wherein actuating the reactant delivery system includes rotatating a screw having an outwardly-extending helical thread positioned to convey the reactants to the reaction zone.

19. The method of claim 18 wherein transferring the heat from the product includes transferring the heat through the screw via conduction.

20. The method of claim 18 wherein a volume between neighboring threads of the screw decreases in a direction toward the reaction zone, and wherein actuating the reactant delivery system includes compacting the reactants as the screw rotates.

* * * * *

UNITED STATES PATENT AND TRADEMARK OFFICE
CERTIFICATE OF CORRECTION

PATENT NO. : 8,624,072 B2
APPLICATION NO. : 13/481682
DATED : January 7, 2014
INVENTOR(S) : Roy Edward McAlister It is certified that error appears in the above-identified patent and that said Letters Patent is hereby corrected as shown below:

On the Title Page

On page 3, in column 1, Item (56) under "Other Publications", line 27, delete "2011" and insert -- 2013 --, therefor.

On page 3, in column 2, Item (56) under "Other Publications", line 65, delete "Technoloigy" and insert -- Technology --, therefor.

On page 4, in column 2, Item (56) under "Other Publications", line 11, delete ""Collodial" and insert -- "Colloidal --, therefor.

On page 4, in column 2, Item (56) under "Other Publications", line 16, delete "behven" and insert -- between --, therefor.

In the Specification

In column 1, line 13, delete "REMOVEAL" and insert -- REMOVAL --, therefor.

In column 4, line 55, delete "111," and insert -- 111. --, therefor.

In column 4, line 59, after "METHODS"" insert -- , --.

In column 4, line 62, delete "functions," and insert -- functions. --, therefor.

Signed and Sealed this
Seventeenth Day of June, 2014

Michelle K. Lee
*Deputy Director of the United States Patent and Trademark Office*

CERTIFICATE OF CORRECTION (continued)

U.S. Pat. No. 8,624,072 B2

In column 4, line 67, delete "103, hi" and insert -- 103. In --, therefor.

In column 5, line 2, delete "emissivity," and insert -- emissivity. --, therefor.

In column 6, line 2, delete "warn" and insert -- warm. --, therefor.

In column 6, line 30, delete "140, Solid" and insert -- 140. Solid --, therefor.

In column 6, line 48, delete "C" and insert -- G --, therefor.

In column 6, line 48, delete "hi" and insert -- In --, therefor.

In column 6, line 49, delete "C" and insert -- G --, therefor.

In column 6, line 53, delete "sold" and insert -- solid --, therefor.

In column 6, line 54, delete "C)" and insert -- G) --, therefor.

In column 6, line 56, delete "sold" and insert -- solid --, therefor.

In column 6, line 60, delete "sold" and insert -- solid --, therefor.

In column 6, line 62, delete "sold" and insert -- solid --, therefor.

In column 6, line 67, delete "reaction, in" and insert -- reaction. In --, therefor.

In column 8, line 45, delete "111" and insert -- 111. --, therefor.

In column 10, line 20, delete "TRANSPORT;" and insert -- TRANSPORT. --, therefor.

In the Claims

In column 12, line 5, in claim 17, delete "rotatating" and insert -- rotating --, therefor.

In column 12, line 9, in claim 18, delete "rotatating" and insert -- rotating --, therefor.